(12) United States Patent
Silva et al.

(10) Patent No.: US 6,344,188 B1
(45) Date of Patent: Feb. 5, 2002

(54) WRINKLE REDUCING CREAM

(75) Inventors: Victor Silva; Bryan K. Harris, both of Troy, IL (US); Gregory J. Rudroff, Florissant; Andrew W. Szczesiul, St. Louis, both of MO (US)

(73) Assignee: Victor Silva, Inc., MO (US)

( * ) Notice: Subject to any disclaimer, the term of this patent is extended or adjusted under 35 U.S.C. 154(b) by 0 days.

(21) Appl. No.: 09/516,325

(22) Filed: Mar. 1, 2000

(51) Int. Cl.$^7$ ................................................ A61K 31/74
(52) U.S. Cl. ................................ 424/78.03; 424/78.02; 424/78.08; 424/401; 514/844; 514/846; 514/847; 514/969
(58) Field of Search ................................ 514/969, 846, 514/847, 844; 424/401, 78.02, 78.03, 78.08

(56) References Cited

U.S. PATENT DOCUMENTS

| | | | | |
|---|---|---|---|---|
| 5,151,270 A | * | 9/1992 | Grimberg | 424/401 |
| 5,296,241 A | * | 3/1994 | Brimberg et al. | 424/682 |
| 5,310,556 A | * | 5/1994 | Ziegler | 424/401 |
| 5,360,824 A | | 11/1994 | Barker | 424/680 |
| 5,523,090 A | * | 6/1996 | Znaiden et al. | 424/401 |
| 5,525,344 A | * | 6/1996 | Wivell | 424/401 |
| 5,560,904 A | * | 10/1996 | Laugier et al. | 424/78.08 |
| 5,626,854 A | | 5/1997 | Ichii | 424/401 |
| 5,667,793 A | | 9/1997 | Cho | 424/401 |
| 5,922,331 A | * | 7/1999 | Mausner | 424/401 |

FOREIGN PATENT DOCUMENTS

JP  0802696 A  *  1/1996

* cited by examiner

*Primary Examiner*—Thurman K. Page
*Assistant Examiner*—Charesse L. Evans
(74) *Attorney, Agent, or Firm*—Don W. Weber

(57) ABSTRACT

A wrinkle reducing cream is presented which reduces wrinkles upon topical application to the skin. The main ingredients of the composition include a water and caffeine composition which is mixed together in a first vessel and a glycerin composition heated in a second vessel. The three components of the active ingredient are mixed carefully, making sure that any precipitate produced is remixed into the solution. After heating and mixing the components, the entire composition is cooled with care being taken to push any precipitate back into solution to ensure an even distribution of all of the components. The active ingredient thus produced may be combined with a suitable cosmetic vehicle to provide the topical wrinkle reducing composition. The composition is topically applied to the wrinkled area over a period of days or months in order to reduce or entirely eliminate wrinkles from the skin. The final active ingredient may also be used for other applications.

8 Claims, No Drawings

WRINKLE REDUCING CREAM

BACKGROUND OF THE INVENTION

This invention relates to the field of cosmetic compositions. More particularly, a unique skin cream is presented which, when used topically, reduces wrinkles without the use of any abrasives or fillers.

Cosmetics such as skin creams and moisturizing creams have been known in the art for hundreds of years. These creams or other moisturizers are applied to the skin in order to moisturize the skin and to prevent chapping or other undesirable conditions of the skin. On occasion, attempts have been made to create a cream or other cosmetic composition which will reduce wrinkles on the face, hands, and other areas of the skin. However, these compositions usually include abrasives which are used to scrape away the wrinkles on the skin. One such abrasive type cream is found in the 1994 patent issued to Barker.

Barker disclosed a human skin cleansing and wrinkle reducing cream comprised of soluble granules in a petroleum jelly or oil base. As described in Barker, the common practice in this art is to use abrading granules to strip off the wrinkled outer layer of skin. Skin abrading formulations are set out in the Barker patent. Barker himself discloses the use of "a plurality of water soluble, skin abrading granules or particles". It is an object of this invention to provide a wrinkle reducing cream which does not require the use of abrading granules or fillers which may irritate the skin.

Although some plant extracts and chemicals have been used in an attempt to create a wrinkle reducing composition, most have met with limited success. A typical example of a skin care composition (used for treating cellulite) is found in the 1997 patent issued to Cho. This patent, U.S. Pat. No. 5,667,793, utilized certain exotic plant extracts as anti-cellulite agents. Cho utilizes a xanthine compound found in the exotic plant extracts to produce an anti-cellulite cream. Cho also discloses the topical application of his cream in order to eliminate or reduce cellulite. However, the general plant extracts used in Cho were designed to reduce cellulite rather than to eliminate wrinkles. Furthermore, the mere use of a xanthine derivative, without the proper cosmetic vehicle, leaves much to be desired with respect to the use of a member of the xanthine family to reduce wrinkles on the skin. It is a further object of this invention to provide a topical cream utilizing any member of the xanthine family in combination with water, glycerin and a suitable cosmetic vehicle to produce a wrinkle reducing cream.

Xanthine derivatives have also been utilized as a bath composition to give a moist or fresh feeling to the skin and a warm feeling to the body. However, the combination of a xanthine with water, glycerin and a suitable cosmetic vehicle can also produce startling and new results, particularly with respect to the reduction of wrinkles on the skin. These new results are only obtained by utilizing the xanthine derivative with water and glycerin brought to a particular consistency of composition by heating and cooling the various elements and combining them in particular proportions. It is a still further object of this invention to produce a wrinkle reducing cream by combining water, a xanthine derivative, and glycerin in a particular stepped method utilizing both heating and cooling of the component parts.

Other and further objects will become apparent upon reading the below described Specification.

SUMMARY OF THE INVENTION

Anhydrous caffeine, a xanthine derivative, is mixed with water and glycerin to form a wrinkle reducing topical cream. The caffeine and water are mixed together first and may be heated to facilitate thorough mixing. Glycerin is heated in another vessel and is added to the caffeine-water solution slowly. The entire composition is then cooled. Any precipitate coming out of the solution during cooling is pushed back into solution. The active ingredient for the topical wrinkle reducing cream is then produced. This active ingredient may then be combined with a suitable cosmetic vehicle to create the topical cream applied to the skin to reduce or eliminate wrinkles. The active ingredient may also be utilized for other purposes.

DETAILED DESCRIPTION OF THE PREFERRED EMBODIMENT

The preferred embodiment includes a composition of caffeine, water, and glycerin. These three key components are combined in particular steps to produce the active ingredient which is to be marketed under the trademark name "Bruvian Complex"™. The "Bruvian Complex"™ will then be combined with a suitable cosmetic vehicle to produce the finished topical wrinkle reducing cream.

This skin cream is noted by the marked absence of aminophylin, a derivative of caffeine. While aminophylin may have some properties which have a salutary effect on the reduction of wrinkles, aminophylin is a prescription drug and the amount of that active ingredient (20%) required to produce an adequate wrinkle cream may be in excess of standards required for the health and welfare of the end user.

It should also be noted that this particular composition of ingredients contains no retinol. Although retinol has been tried in the past with respect to moisturizing and wrinkle reducing properties, retinol may cause harm to the end user. Since it is likely that women will use this wrinkle reducing cream, it would be highly desirable to develop a wrinkle reducing cream without using retinol. It is a still further object of this invention to provide a wrinkle reducing cream which utilizes neither aminophylin nor retinol as an ingredient in the final composition.

The preferred procedure for making the active ingredient of this disclosure involves nine steps, combining and heating the various components to produce the final composition. The steps to be followed in producing this active ingredient are as follows.

1. Into a first vessel, one places 60 ml of water, in proportion, and 74 grams of anhydrous caffeine, in proportion. This vessel may be heated to facilitate thorough mixing.
2. The caffeine and water are mixed together. At the same time the temperature of this mixture may be brought up to approximately 70 degrees Centigrade.
3. The water and caffeine are slowly stirred to produce a homogenous mixture.
4. While the watercaffeine mixture is being prepared, a second vessel containing 167 grams of glycerin, in proportion, is heated.
5. The glycerin in the second vessel is heated to a temperature of approximately 70 degrees Centigrade.
6. Once the glycerin is heated to 70 degrees Centigrade, the glycerin is slowly added to the water-caffeine mixture. This is accomplished by slowly stirring the glycerin as it is added to the first vessel containing the water-caffeine mixture.
7. The water-caffeine and glycerin compositions are slowly mixed for approximately one and one-half minutes, while any precipitate is pushed back into the mixture.

8. After mixing the composition for approximately one and one-half minutes, the mixture is removed from heat and allowed to cool at room temperature. A cold water bath can be used to speed up the precipitation and cooling process.

9. A precipitate may be produced as the mixture is cooled and comes out of the solution. Any precipitate must be mixed back into the entire solution in order to keep all components evenly distributed throughout the final composition.

These nine steps produce the active ingredient, called the "Bruvian Complex"™. This active ingredient may then be combined with a suitable cosmetic vehicle to produce the topical wrinkle reducing cream. In the production of this particular active ingredient, the general parameters set out above could be combined to produce approximately 250 grams of the active ingredient. The actual yield of the final composition would depend on the total weight of the ingredients used less the amount of water lost during the heating process.

During this process, most of the water is lost due to evaporation. Using the weights indicated above (60 ml or grams of water, 74 grams of anhydrous caffeine and 167 grams of glycerin) the final active ingredient would contain 4% by weight of water, 29.5% by weight of caffeine and 66.5% by weight of glycerin.

The above weights are meant as an illustration only and not as a limitation. The amounts of water, caffeine, and glycerin are proportional. For example, one could produce 2,500 grams of active ingredient by adding 600 ml of water 740 grams of anhydrous caffeine and then mixing with 1,670 grams of glycerin.

Certain broad parameters can be described in practicing this invention which will produce an effective active ingredient. The above weights of water, caffeine, and glycerin are meant as a means of illustration only and not as a limitation. The following parameters can be used in producing the active ingredient. Generally, the active ingredient can be produced by mixing the following range of components by weight at the temperatures indicated:

1. The amount of water used in the first vessel could be between 90 ml to 900 ml. To that could be added between 10 grams to 600 grams of caffeine.
2. The water-caffeine mixture may be heated to between 48.8 degrees Centigrade to 115 degrees Centigrade in the first vessel to facilitate mixing.
3. These components should be mixed until the caffeine goes into solution.
4. The glycerin to be added to the first vessel could range from between 45 grams to 540 grams of glycerin.
5. The temperature range for heating the glycerin in the second vessel can be from 10 degrees Centigrade to 115 degrees Centigrade.
6. Once these two vessels have been prepared, the glycerin is added to the water-caffeine solution slowly.
7. In order to mix the water-caffeine and glycerin components, approximately one and one-half minutes are required. Any precipitate should be pushed back into solution. However, these three components can be mixed from between 15 seconds to 10 minutes to still produce a suitable final composition.
8. The combined final mixture is then allowed to cool.
9. As the above mixture is cooled, the precipitate should be mixed back into the whole in order to keep all components evenly distributed throughout the mass of the active ingredient.

The active ingredient produced by this method will produce an active ingredient containing water, caffeine, and glycerin. It has been found that the following range of percentages by weight of each of the initial components produces a satisfactory final active ingredient: Final Percentage by Weight—water 4% to 20%; caffeine 14% to 50%; glycerin 30% to 82%.

The percentage by weight of water, caffeine and glycerin set out above produce a suitable active ingredient having wrinkle reducing and other properties.

Once the active ingredient has been produced, it should be combined with a suitable cosmetic vehicle which would normally be some type of ointment base. Suitable cosmetic vehicles may include hydrophyllic ointments, petrolatums such as Vaseline™, Dermabase™ or standard cold creams found commonly in the market. In normal practice the active ingredient would be heated and combined with the suitable cosmetic base to produce the final composite cream. It is the active ingredient or "Bruvian Complex"™ which forms the essence of this new composition of matter.

It has been found that the combination of water, caffeine and glycerin, obtained through the procedures as described above, produces a highly effective wrinkle reducing cream capable of reducing or eliminating wrinkles when topically applied. The instant composition is an improvement over those composition involving caffeine alone or caffeine in composition with other cosmetic vehicles. Caffeine compositions alone would dissolve in water, whereas the instant composition does not dissolve in water. This is important as the instant composition will not deteriorate or wash off during bathing or heavy sweating. Another salutary effect of the instant device is that it reactivates with water rather than dissolves in water.

After much experimentation it has been found that the use of glycerin to combine with the caffeine is important since glycerin is much more suitable than animal fat or any other dissolving agent. Glycerin is more stable than animal fat and will not allow the caffeine to penetrate into the actual cells sought to be treated with this final compound. Although the water-caffeine-glycerin components must be mixed and heated as described above, the end result is a highly desirable skin cream that has been effective in actual clinical tests in reducing wrinkles.

It is thought that the instant composition provides the salutary effects of a wrinkle reducing cream by strengthening the cell membrane and coating the cell membranes with strands of fat to protect cells which would otherwise produce wrinkles. Although the exact mechanism action of this new composition has not been determined, experimentation has shown that the combination of water, caffeine and glycerin, when heated, mixed, and cooled, as outlined above, will produce a cream which will reduce wrinkles.

The final composite wrinkle cream should be applied twice daily to the wrinkled areas. Results have been seen as soon as 24 hours after a first application, although the best results are obtained over a period of days or months of application of the wrinkle cream.

We claim:

1. A method of producing a composition of matter, comprising the steps of:
   1) placing between 90 ml to 900 ml of water and 10 grams to 600 grams of caffeine into a first vessel;
   2) mixing the water and caffeine components together;
   3) slowly mixing the water and caffeine components together;
   4) placing between 45 grams to 540 grams of glycerin into a second vessel;

5) heating the second vessel containing the glycerin to a temperature range between 10 degrees Centigrade and 115 degrees Centigrade;
6) slowly adding the heated glycerin in vessel 2 to the water-caffeine mixture while stirring the composite solution;
7) mixing the water, caffeine and glycerin components slowly for a certain period of time, ranging between 15 seconds to 10 minutes, while pushing any precipitate back into the mixture;
8) removing the resulting final composite solution from the heat and allowing it to cool to room temperature;
9) mixing any precipitate that develops in Step 8 back into the composition in order to keep the precipitate evenly distributed, producing the active ingredient herein;
10) combining the resulting active ingredient with a suitable cosmetic vehicle to produce a topical wrinkle reducing cream;
whereby said water, caffeine and glycerin chemically interact to create a final active ingredient.

2. A method of producing a composition of matter as in claim 1, wherein said first vessel containing the water-caffeine mixture may be heated to between 48.8 degrees Centigrade to 115 degrees Centigrade to facilitate mixing.

3. A method of producing a composition of matter, comprising the steps of:
1) placing in proportion, 60 ml of water and 74 grams of anhydrous caffeine into a first vessel;
2) mixing the water and caffeine components together;
3) slowly mixing the water and caffeine together in the first vessel until the caffeine goes into solution;
4) placing in proportion, 167 grams of glycerin into a second vessel;
5) heating the second vessel containing the glycerin to 70 degrees Centigrade;
6) slowly adding the heated glycerin in vessel 2 to the water-caffeine mixture while stirring the resulting composite solution;
7) mixing the water, caffeine and glycerin components slowly for one and one-half minutes, while pushing any precipitate back into the mixture;
8) allowing the resulting composite solution from the heat and allowing it to cool to room temperature;
9) mixing any precipitate that develops in Step 8 back into the composition solution in order to keep the precipitate evenly distributed, producing the active ingredient herein;
10) combining the resulting active ingredient with a suitable cosmetic vehicle to produce a topical wrinkle reducing cream;
whereby said water, caffeine and glycerin chemically interact to create a final active ingredient.

4. A method of producing a composition of matter as in claim 3, wherein said first vessel containing the water-caffeine mixture may be heated to approximately 70 degrees Centigrade to facilitate mixing.

5. The method of producing a composition of matter as in claim 1, wherein said suitable cosmetic vehicle includes a hydrophilic ointment, a petrolatum or cold cream.

6. A method of producing a composition of matter as in claim 3, wherein said suitable cosmetic vehicle includes a hydrophilic ointment, a petrolatum or cold cream.

7. A composition of matter, consisting essentially:
1. Between 4% to 20% by weight of water;
2. Between 14% to 50% by weight of caffeine;
3. Between 30% to 82% by weight of glycerin;
wherein said water and caffeine are placed in a first vessel and mixed together and wherein said glycerin is heated in a second vessel and then added to said water and caffeine mixture and then cooled;
whereby said water, caffeine and glycerin chemically interact to create a final active ingredient.

8. A composition of matter as in claim 5, wherein said composition consists essentially of 4% by weight of water, 14% to 50% be weight of caffeine, and wherein the remainder of said composition is glycerin; and wherein said water and caffeine are placed in a first vessel and mixed together and wherein said glycerin is heated in a second vessel and then added to said water and caffeine mixture and then cooled;
whereby said water, caffeine and glycerin chemically interact to create a final active ingredient.

* * * * *